United States Patent
Berg

[11] Patent Number: 5,897,750
[45] Date of Patent: Apr. 27, 1999

[54] SEPARATION OF ACETONE FROM ISOPROPANOL-WATER MIXTURES BY EXTRACTIVE DISTILLATION

[76] Inventor: Lloyd Berg, 1314 S. 3rd Ave., Bozeman, Mont. 50715

[21] Appl. No.: 08/919,404

[22] Filed: Aug. 28, 1997

[51] Int. Cl.[6] .............................. B01D 3/40; C07C 45/83
[52] U.S. Cl. .............................. 203/57; 203/14; 203/58; 203/59; 203/60; 203/62; 203/63; 203/64; 203/65; 203/67; 203/68; 203/69; 203/70; 568/41; 568/913; 568/916
[58] Field of Search ............................ 203/57–60, 62–65, 203/67–70, 14, 18; 568/410, 913, 916, 411

[56] References Cited

U.S. PATENT DOCUMENTS

| | | | |
|---|---|---|---|
| 3,764,627 | 10/1973 | Prinz | 568/411 |
| 3,955,939 | 5/1976 | Sommer et al. | 568/896 |
| 3,990,952 | 11/1976 | Katzan et al. | 203/37 |
| 4,113,780 | 9/1978 | Strehlke et al. | 203/62 |
| 4,459,179 | 7/1984 | Berg et al. | 203/58 |
| 4,510,022 | 4/1985 | Berg et al. | 203/57 |
| 4,511,437 | 4/1985 | Heck et al. | 203/79 |
| 4,566,948 | 1/1986 | Berg et al. | 203/58 |
| 4,584,063 | 4/1986 | Berg et al. | 203/60 |
| 4,620,901 | 11/1986 | Berg et al. | 203/63 |
| 4,666,560 | 5/1987 | Berg et al. | 203/57 |
| 4,675,080 | 6/1987 | Berg et al. | 203/64 |
| 4,696,720 | 9/1987 | Kiser | 203/DIG. 13 |
| 4,718,987 | 1/1988 | Berg et al. | 203/60 |
| 5,085,739 | 2/1992 | Berg | 203/64 |
| 5,470,443 | 11/1995 | Berg | 203/57 |

FOREIGN PATENT DOCUMENTS

| | | | |
|---|---|---|---|
| 531419 | 10/1956 | Canada | 203/69 |
| 669029 | 8/1963 | Canada | 203/62 |
| 485485 | 5/1938 | United Kingdom | 203/63 |
| 687171 | 2/1953 | United Kingdom | 203/69 |
| 696040 | 8/1953 | United Kingdom | 203/69 |
| 967471 | 8/1964 | United Kingdom | 203/60 |

*Primary Examiner*—Virginia Manoharan

[57] ABSTRACT

Acetone cannot be separated from a mixture of isopropanol and water because of the closeness of their boiling points. Acetone can be easily separated from isopropanol and water by extractive distillation. Effective extractive agents are 1-nitropropane, 3-carene, dimethylsulfoxide and 3-pentanone.

1 Claim, No Drawings

SEPARATION OF ACETONE FROM ISOPROPANOL-WATER MIXTURES BY EXTRACTIVE DISTILLATION

FIELD OF THE INVENTION

This invention relates to a method for separating acetone from a mixture of acetone, isopropanol and water using certain organic compounds as the agent in extractive distillation.

DESCRIPTION OF PRIOR ART

Extractive distillation is the method of separating close boiling comnounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Celcius degrees or more higher than the highest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

The usual method of evaluating the effectiveness of extractive distillation agents is the change in relative volatility of the compounds to be separated. Table 1 shows the degree of separation or purity obtainable by theoretical plates at several relative volatilities. Table 1 shows that a relative volatility of at least 1.2 is required to get an effective separation by rectification.

TABLE 1

Effect of Relative Volatility on Theoretical Stage Requirements.

| Separation Purity, | Relative Volatility | | | | | | | |
|---|---|---|---|---|---|---|---|---|
| Both Products (Mole Fraction) | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

Acetone and the isopropanol—water azeotrope boil fourteen degrees apart and are difficult to separate by conventional rectification. Table 2 shows that to get 99% purity, with a relative volatility of 2, sixteen actual plates are required, with a relative volatility of 3, only ten actual plates are required.

TABLE 2

Theoretical and Actual Plates Required vs. Relative Volatility For Acetone - Isopropanol - Water Separation

| Relative Volatility | Theoretical Plates Required At Total Reflux, 99% Purity | Actual Plates Required, 75% Eff. |
|---|---|---|
| 1.1 | 95 | 127 |
| 2.0 | 12 | 16 |
| 3.0 | 7 | 10 |

OBJECTIVE OF THE INVENTION

The object of this invention is to provide a process or method of extractive distillation that will enhance the relative volatility of acetone to isopropanol and water in their separation in a rectification column. It is a further object of this invention to identify effective extractive distillation agents that are stable and can be recycled.

SUMMARY OF THE INVENTION

The objects of this invention are provided by a process for the separation of acetone from isopropanol and water which entails the use of certain organic compounds when employed as the agent in extractive distillation.

TABLE 3

Effective Extractive Distillation Gents For Separating Acetone From Acetone - Isopropanol - Water Mixtures

| Compound | Relative Volatility |
|---|---|
| None | 1.07 |
| Dimethylsulfoxide | 3.0 |
| Butyl acetate | 3.0 |
| Hexyl formate | 2.2 |
| Methyl pivalate | 3.0 |
| Propyl butyrate | 2.9 |
| Isopropyl phthalate | 3.0 |
| Diethylene glycol | 3.0 |
| Polyethylene glycol 300 | 2.2 |
| Heptane | 3.0 |
| Ethyl benzoate | 2.0 |
| Methyl t-butyl ether | 3.0 |
| Isopropyl ether | 3.0 |
| Phenyl ether | 2.2 |
| Formamide | 2.0 |
| Anisole | 2.0 |
| Polyethylene qlycol 400 | 3.0 |
| 4-Methyl-2-pentanone | 3.0 |
| 2-Heptanone | 2.4 |
| 2-Octanone | 2.8 |
| 2-Undecanone | 2.7 |
| Dimethyl carbonate | 2.6 |
| 2-Butanone | 2.5 |
| Tetra methyl sulfone | 2.1 |
| Butyl formate | 3.0 |
| Butyl benzoate | 2.0 |
| Butyl ether | 2.8 |
| n-Pentyl propionate | 2.7 |
| Dimethyl formamide | 2.8 |
| 2-Methoxyethanol | 2.6 |
| Propylene glycol phenyl ether | 2.5 |
| 1,1,3,3-Tetramethyl urea | 3.0 |
| Butyronitrile | 2.0 |
| 2-Ethoxyethanol | 3.0 |
| 1-Methoxy-2-propanol | 3.0 |
| Diethylene glycol methyl ether | 2.8 |
| Diisobutyl carbinol | 2.5 |
| 3-Ethoxy propionate | 2.4 |
| Diethylene glycol ethyl ether | 2.4 |
| Diethylene glycol hexyl ether | 2.3 |

TABLE 3-continued

Effective Extractive Distillation Gents For Separating
Acetone From Acetone - Isopropanol - Water Mixtures

| Compound | Relative Volatility |
|---|---|
| Diethylene glycol butyl ether | 2.6 |
| Tripropylene glycol methyl ether | 2.8 |
| 3-Methyl-2-butanone | 2.3 |
| 2-Pentanone | 2.6 |
| 3-Pentanone | 3.0 |
| 4-Methyl-2-pentanone | 2.9 |
| 2,6-Dimethyl-4-heptanone | 2.5 |
| 5-Methyl-2-hexanone | 2.5 |
| 1,3-Butanediol | 2.1 |
| 1,4-Butanediol | 2.1 |
| Ethylene glycol | 2.3 |
| 2-Methyl-2,4-pentanediol | 2.1 |
| 2,3-Butanediol | 2.1 |
| Methyl benzoate | 2.6 |
| Ethyl acetate | 2.3 |
| Isobornyl acetate | 2.1 |
| Methyl propionate | 2.5 |
| Isocetyl stearate | 3.0 |
| Dioctyl phthalate | 2.0 |
| Dibutyl sebacate | 3.0 |
| 1-Methoxy-2-propanol | 3.0 |
| Cyclohexanol | 2.3 |
| 3-Methyl-2-butanol | 3.0 |
| Amyl alcohol | 2.1 |
| 4-Methyl-2-pentanol | 2.7 |
| n-Hexanol | 2.4 |
| n-Octanol | 2.2 |
| n-Tetradecanol | 3.0 |
| Sulfolane | 2.3 |
| Tetraethyl silicate | 3.0 |
| 1-Methyl piperazine | 2.5 |
| Toluene | 2.0 |
| Ethyl benzene | 2.0 |
| o-Xylene | 2.0 |
| m-Xylene | 2.3 |
| p-Xylene | 2.7 |
| Dipentene | 2.5 |
| Cumene | 2.8 |
| Cyclohexene | 3.0 |
| Limonene | 3.0 |
| 2,2,4-Trimethyl pentane | 2.7 |
| 4-Hydroxy-2-methyl-2-pentanone | 2.3 |
| Cyclohexane | 2.7 |
| 3-Carene | 3.0 |
| Methyl glutaronitrile | 2.6 |
| 2,2-Dimethoxypropane | 3.0 |
| Propylene glycol methyl ether | 2.6 |
| 2-Amino-2-methyl-1-propanol | 2.2 |
| Acetal | 2.0 |
| Triethanolamine | 2.8 |
| Ethanolamine | 2.0 |
| N,N-Dimethyl aniline | 2.1 |
| 1-(2-Hydroxyethyl-2-pyrrolidinone | 2.9 |
| 4-Ethyl morpholine | 2.8 |
| 2,6-Diethyl morpholine | 2.4 |
| Cyclohexylamine | 3.0 |
| Diethylamine | 3.0 |
| Triethylamine | 3.0 |
| Butyl amine | 3.0 |
| Diisobutylamine | 3.0 |
| N,N-Dimethyl ethanolamine | 2.3 |
| 3-Dimethyl aminopropylamine | 2.0 |
| Propiophenone | 2.1 |
| Diaminocyclohexane | 2.8 |
| 2-Dimethylamino-2-methyl-1-propanol | 3.0 |
| Hexamethylene imine | 3.0 |
| 2-Methyl-1-butanol | 2.4 |
| 3-Methyl-1-butanol | 2.3 |
| 3-Methyl-2-butanol | 2.3 |
| 1-Nitropropane | 2.3 |

DETAILED DESCRIPTION OF THE INVENTION

I have discovered that certain organic compounds will effectively increase the relative volatility between acetone and isopropanol—water during rectification when employed as the agent in extractive distillation. Table 3 summarizes the data obtained with these agents. They are dimethylsulfoxide, butyl acetate, hexyl formate, methyl pivalate, propyl butyrate, isopropyl phthalate, diethylene glycol, polyethylene glycol 300, polyethylene glycol 400, heptane, ethyl benzoate, methyl t-butyl ether, isopropyl ether, phenyl ether, formamide, anisole, 4-methyl-2-pentanone, 2-heptanone, 2-octanone, 2-undecanone, dimethyl carbonate, 2-butanone, tetramethyl sulfone, butyl formate, butyl benzoate, butyl ether, n-pentyl propionate, dimethyl formamide, 2-methoxyethanol, propylene glycol phenyl ether, 1, 1, 3, 3-tetramethyl urea, butyronitrile, 2-ethoxyethanol, 1-methoxy-2-propanol, diethylene glycol methyl ether, diisobutyl carbinol, 3-Ethoxy propionate, diethylene glycol ethyl ether, diethylene glycol hexyl ether, diethylene glycol butyl ether, tripropylene glycol methyl ether, 3-methyl-2-butanone, 2-pentanone, 3-pentanone, 4-methyl-2-pentanone, 2,6-dimethyl-4-heptanone, 5-methyl-2-hexanone, 1,3-butanediol, 1,4-butanediol, ethylene glycol, 2-methyl-2,4-pentanediol, 2,3-butanediol, methyl benzoate, ethyl acetate, isobornyl acetate, methyl propionate, isocetyl stearate, dioctyl phthalate, dibutyl sebacate, 1-methoxy-2-propanol, cyclohexanol, 3-methyl-2-butanol, amyl alcohol, 4-methyl-2-pentanol, n-hexanol, n-octanol, n-tetradecanol, sulfolane, tetraethyl silicate, toluene, 1-methyl piperazine, ethyl benzene, o-xylene, m-xylene, p-xylene, dipentene, cumene, cyclohexene, limonene, 2,2,4-trimethyl pentane, 4-hydroxy-2-methyl-2-pentanone, cyclohexane, 3-carene, methyl glutaronitrile, 2,2-dimethoxypropane, propylene glycol methyl ether, 2-amino-2-methyl-l-propanol, acetal. triethanolamine, ethanolamine, N,N-dimethyl aniline, 1-(2-hydroxyethyl)-2-pyrrolidinone, 4-ethyl morpholine, 2,6-diethyl morpholine, cyclohexylamine, diethylamine, triethylamine, butyl amine, diisobutylamine, N,N-dimethylethanolamine, 3-dimethyl aminopropyl amine, propiophenone, diaminocyclohexane, 2-dimethylamino-2-methyl-1-propanol, hexamethylene imine, 2-methyl-1-butanol, 3-methyl-1-butanol, 3-methyl-2-butanol and 1-nitropropane.

THE USEFULNESS OF THE INVENTION

The usefulness or utility of this invention can be demonstrated by referring to the data presented in Tables 1, 2 and 3. All of the successful agents listed there show that acetone can be separated from isopropanol and water by means of extractive distillation and that the ease of separation as measured by relative volatility is considerable.

WORKING EXAMPLES

Example 1

Fifty grams of acetone, isopropanol and water mixture and 50 grams of 1-nitropropane as the extractive agent were charged to a vapor-liquid equilibrium still and refluxed for three hours. The vapor composition was 2.5% acetone, 76.5% isopropanol and 21.0% water; the liquid composition was 1.05% acetone, 65.4% isopropanol and 33.55% water. This is a relative volatility of acetone to isopropoanol of 2.0.

Example 2

Fifty grams of acetone, isopropanol and water mixture and 50 grams of 3-carene as the extractive agent were charged to a vapor-liquid equilibrium still and refluxed for three hours. The vapor composition was 4.1% acetone, 76.4% isopropanol and 14.5% water; the liquid composition was 1.5% acetone, 84.5% isopropanol and 14% water. This is a relative volatility of acetone to isopropanol of 3.0

I claim:

1. A method for recovering acetone from a mixture consisting of acetone, isopropanol and water which comprises distilling said mixture consisting of acetone, isopropanol and water in the presence of an extractive distillation agent, recovering the acetone as overhead product and obtaining the isopropanol, water and the extractive distillation agent As bottoms product, wherein said extractive distillation agent consists of one material selected from the group consisting of dimethylsulfoxide, butyl acetate, hexyl formate, methyl pivalate, propyl butyrate, isopropyl phthalate, diethylene glycol, heptane, polyethylene glycol 300, ethyl benzoate, methyl t-butyl ether, isopropyl ether, phenyl ether, anisole, polyethylene glycol 400, 4-methyl-2-pentanone, 2-heptanone, 2-octanone, 2-undecanone, 2-butanone, dimetliylcarbonate, tetramethyl sulfone, butyl formate, butyl benzoate, butyl ether, n-pentyl propionate, 2-methoxyethanol, propylene glycol phenyl ether, 1,1,3,3-tetramethyl urea, butyronitrile, 2-ethoxyethanol, 1-methoxy-2-propanol, diethylene glycol methyl ether, diisobutyl carbinol, 3-ethoxy propionate, diethylene glycol ethyl ether, diethylene glycol hexyl ether, diethylene glycol butyl ether, tripropylene glycol methyl ether, 3-methyl-2-butanone, 2-pentanone, 3-pentanone, 4-methyl-2-pentanone, 2,6-dimethyl-4-heptanone, 5-methyl-2-hexanone, 1,3-butanediol, 1,4-butanediol, ethylene glycol, 2methyl-2,4-pentanediol, 2,3-butanediol, methyl benzoate, ethyl acetate, isobornyl acetate, methyl propionate, isocetyl stearate, dioctyl phthalate, dibutyl sebacate, 1-methoxy-2-propanol, cyclohexanol, 3-methyl-2-butanol, amyl alcohol, 4-methyl-2-pentanol, n-hexanol, n-octanol, n-tetradecanol, sulfolane, tetraethyl silicate, 1-methyl piperazine, toluene, ethyl benzene, o-xylene, m-xylene, p-xylene, dipentene, cumene, cyclohexene, limonene, 2,2,4-trimethyl pentane, 4-hydroxy-2-methyl-2-pentanone, cyclohexane, 3-carene, methyl glutaronitrile, acetal, 2,2-dimethoxypropane, propylene glycol methyl ether, triethanolamine, 2-amino 2-methyl-1-propanol, ethanolamine, N,N-dimethyl aniline, 1-(2-hydroxyethyl)-2-pyrrolidinone, 4-ethyl morpholine, cyclohexylamine, 2,6-dimethyl morpholine, diethylamine, triethylamine, butylamine, diisobutylamine, N,N-dimethyl ethanolamine, 3-dimethyl aminopropylamine, propiophenone, diaminocyclohexane, 2-dimethylamino-2-methyl-1-propanol, hexamethylene imine, 2-methyl-1-butanol, 3-methyl-1-butanol, 3-methyl-2-butanol and 1-nitropropane.

* * * * *